(12) United States Patent
Goel et al.

(10) Patent No.: US 11,746,381 B2
(45) Date of Patent: Sep. 5, 2023

(54) METHODS FOR DIAGNOSING AND TREATING GASTRIC CANCER USING MIRNA EXPRESSION

(71) Applicant: Cancer Diagnostics Research Innovations, Colleyville, TX (US)

(72) Inventors: Ajay Goel, Colleyville, TX (US); Daisuke Izumi, Colleyville, TX (US)

(73) Assignee: Cancer Diagnostics Research Innvovations, LLC, Colleyville, TX (US)

( * ) Notice: Subject to any disclaimer, the term of this patent is extended or adjusted under 35 U.S.C. 154(b) by 279 days.

(21) Appl. No.: 16/492,524

(22) PCT Filed: Mar. 9, 2018

(86) PCT No.: PCT/US2018/021713
§ 371 (c)(1),
(2) Date: Sep. 9, 2019

(87) PCT Pub. No.: WO2018/165532
PCT Pub. Date: Sep. 13, 2018

(65) Prior Publication Data
US 2021/0139992 A1 May 13, 2021

Related U.S. Application Data

(60) Provisional application No. 62/469,857, filed on Mar. 10, 2017.

(51) Int. Cl.
*C12Q 1/6886* (2018.01)

(52) U.S. Cl.
CPC ..... *C12Q 1/6886* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 4,275,149 A | 6/1981 | Litman et al. |
| 4,318,980 A | 3/1982 | Boguslaski et al. |
| 4,683,195 A | 7/1987 | Mullis et al. |
| 4,683,202 A | 7/1987 | Mullis |
| 4,737,456 A | 4/1988 | Weng et al. |
| 4,965,188 A | 10/1990 | Mullis |
| 5,143,854 A | 9/1992 | Pirrung et al. |
| 5,384,261 A | 1/1995 | Winkler et al. |
| 5,424,186 A | 6/1995 | Fodor et al. |
| 5,445,934 A | 8/1995 | Fodor et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,789,162 A | 8/1998 | Dower et al. |
| 5,800,992 A | 9/1998 | Fodor et al. |
| 6,040,193 A | 3/2000 | Winkler et al. |
| 6,586,177 B1 | 7/2003 | Shuber |
| 6,645,730 B2 | 11/2003 | Nair |
| 7,252,955 B2 | 8/2007 | Pant et al. |
| 7,312,053 B2 | 12/2007 | Tada et al. |
| 7,871,769 B2 | 1/2011 | Baker et al. |
| 2006/0019270 A1 | 1/2006 | Yang et al. |
| 2007/0202511 A1 | 8/2007 | Chen et al. |
| 2008/0045418 A1 | 2/2008 | Xia |
| 2009/0099034 A1 | 4/2009 | Ahlquist et al. |
| 2010/0075304 A1 | 3/2010 | Raponi et al. |
| 2010/0298410 A1 | 11/2010 | Obad et al. |
| 2011/0039272 A1 | 2/2011 | Cowens et al. |
| 2011/0183859 A1 | 7/2011 | Harris et al. |
| 2011/0318742 A1 | 12/2011 | Sung et al. |
| 2013/0065769 A1 | 3/2013 | Wong |
| 2014/0121133 A1* | 5/2014 | Zhang ............... C12Q 1/6876 506/16 |
| 2015/0254400 A1 | 9/2015 | Lei et al. |

FOREIGN PATENT DOCUMENTS

| | | |
|---|---|---|
| EP | 2196542 | 6/2010 |
| WO | WO 2008/055158 | 5/2008 |
| WO | WO 2009/015357 | 1/2009 |
| WO | WO 2009/111643 | 9/2009 |

(Continued)

OTHER PUBLICATIONS

Tumilson et al. Molecular Neurobiology. 2014. 50: 545-558 (Year: 2014).*
Zhou et al Scientific Reports. Jun. 10, 2015. 6:11251 (Year: 2015).*
Song et al Dig Dis Sci. 2011, 8 pages, available via URL: <gene-quantification.de/song-et-al-microrna-norm-2011.pdf>(Year: 2011).*
Li et al Gut. 2010. 59: 579-585 (Year: 2010).*
Nucleic Acids Research. 2009. 37: 1672-1681 and Supplemental Table 1, 2 pages (Year: 2009).*
Chen et al IUBMB Life. Jul. 2012. 64(7): 628-635 (Year: 2012).*
Ahn, Joong Bae, et al., "DNA Methylation Predicts Recurrence from Resected Stage 3 Proximal Colon Cancer," Cancer, May 1, 2011, 117(9):1847-1854.
Barbarotto, et al., "MicroRNAs and Cancer: Profile, Profile, Profile," International Journal of Cancer, 122: 969-977, 2008.
Bartley, et al., "Complex Patterns of Altered MicroRNA Expression During the Adenoma-Adenocarcinoma Sequence for Microsatellite-Stable Colorectal Cancer," Clinical Cancer Research, 17(23): 7283-7293, 2011.

(Continued)

*Primary Examiner* — Carla J Myers

(57) ABSTRACT

Dysregulated expression of microRNAs (miRNAs) has emerged as a hallmark feature in human cancers. Aspects of the disclosure relate to methods for selecting optimal therapy for a patient from several alternative treatment options. A major clinical challenge in cancer treatment is to identify the subset of patients who will benefit from a therapeutic regimen, both in metastatic and adjuvant settings. The number of anti-cancer drugs and multi-drug combinations has increased substantially in the past decade, however, treatments continue to be applied empirically using a trial-and-error approach. Here methods and compositions are provided to determine the optimal treatment option for gastric cancer patients.

9 Claims, No Drawings

(56) References Cited

FOREIGN PATENT DOCUMENTS

| WO | WO 2011/128900 | 10/2011 |
|---|---|---|
| WO | WO 2016/160882 | 10/2016 |

OTHER PUBLICATIONS

Burke et al., "Colorectal Liver Metastases," Postgrad Med J, 1996, vol. 72, pp. 464-469.
Chan, Jennifer A., et al., "MicroRNA-21 is an Antiapoptotic Factor in Human Glioblastoma Cells," Cancer Res., Jul. 15, 2005, 65:(14) 6029-6033.
Chen, Caifu, et al., "Real-Time Quantification of MicroRNAs by Stem-Loop RT-PCR," Nucleic Acids Research, (2005), vol. 33, No. 20, 9 pages.
Chen, Xi, et al., "Characterization of MicroRNAs in senim: A Novel Class of Biomarkers for Diagnosis of Cancer and other Diseases," Cell Research, (2008), 18:997-1066.
Cheng, et al., "Circulating Plasma MiR-141 Is a Novel Biomarker for Metastatic Colon Cancer and Predicts Poor Prognosis," PLoS One, 2011, 6(3):e17745. Doi:10.1371/journal.pone.0017745.
Choi et al., "Hypomethylation of LINE-1 and Alu in Well-Differentiated Neuroendocrine Tumors (Pancreatic Endocrine Tumors and Carcinoid Tumors," Modern Pathology, 2007, vol. 20, pp. 802-810.
Cruickshanks et al., "Isolation of Cancer-Specific Chimeric Transcripts Induced by Hypomethylation of the Line-1 Antisense Promoter," Genomics, 2009, vol. 94, pp. 397-406.
Database Biosis, [Online], Hur et al., "Identification of a Novel Metastasis-Specific miRNA Signature in Human Colorectal Cancer," 2015, XP002692684, retrieved from BIOSIS.
Du, Pan, et al., "Lumi: A Pipeline for Processing Illumina Microarray," Bioinformatics, vol. 24, No. 13, (2008), pp. 1547-1548.
Extended European Search Report Issued in European Patent Application No. 12859326.6, dated Nov. 19, 2015.
Figueiredo et al., "Global DNA Hypomethylation (LINE-1) in the Normal Colon and Lifestyle Characteristics and Dietary and Genetic Factors," Cancer Epidemiol Biomarkers Prev, 2009, vol. 18, pp. 1041-1049.
Graser, A., et al., "Comparison of CT Colonography, Colonoscopy, Sigmoidoscopy and Faecal Occult Blood Tests for the Detection of Advanced Adenoma in an Average Risk Population," Gut, (2009), 58:241-248.
Greiner, et al., "Principles and Practical Application of the Receiver-Operating Characteristic Analysis for Diagnostic Tests," *Preventive Veterinary Medicine*, 45: 23-41, 2000.
Guo, et al., "Differential Expression of microRNA Species in Human Gastric Cancer Versus Non-Tumorous Tissue," Journal of Gastroenterology and Hepatology, 24(4): 652-657, 2009.
Huang, et al., "MicroRNA expression profile in non-cancerous colonic tissue associated with lymph node metastasis of colon cancer." Journal of Digestive Diseases (Impact Factor: 1.85). Sep. 2009; 10(3):188-94.
Hui, Angela, et al., "Robust Global Micro-RNA Profiling with Formalin-Fixed Paraffin-Embedded Beast Cancer Tissues," Laboratory Investigation, (2009), 89, pp. 597-606.
Hunter, Melissa Piper, et al., "Detection of MicroRNA Expression in Human Peripheral Blood Microvesicles," PLOS One, Nov. 2008, vol. 3, Issue 11, 11 pages.
Hur, K. et al "Identification of a Novel Metastasis-Specific miRNA Signature in Human Colorectal Cancer" Digestive Disease Week, May 19-22, 2012, Gastroenterology, May 2012, vol. 142, No. 5, Supplement 1, pp. S525-S526; Meeting Abstract.
Hur, K. et al. "Abstract 95: Increased hypomethylation of LINE-1 and Alu in human colorectal cancer metastasis" Proceedings of the 102$^{nd}$ Annual Meeting of the American Association for Cancer Research; Apr. 2-6, 2011, Cancer Research Apr. 15, 2011, vol. 71, Issue 8, Supplement 1.

Imperiale, Thomas F., et al., "Fecal DNA Versus Fecal Occult Blood for Colorectal-Cancer Screening in an Average-Risk Population," The New England Journal of Medicine, Dec. 23, 2004, 351 :2704-2714.
International Preliminary Report on Patentability Issued in Corresponding PCT Patent Application No. PCT/US2018/021713, dated Sep. 10, 2019.
International Search Report and Written Opinion Issued in Corresponding PCT Patent Application No. PCT/US2018/021713, dated May 16, 2018.
International Search Report for PCT/US2010/052112, dated Jun. 7, 2011, 4 pages.
Jemal, et al., "Cancer Statistics," CA Cancer J. Clin., (2007);57;43-66.
Kim, et al., "miRNA Signature Associated with Outcome of Gastric Cancer Patients Following Chemotherapy," *BMC Medical Genomics*, 4(79): 1-13, 2011.
Kwon, Hyeong-Ju, et al., "DNA Methylation Changes in Ex-Adenoma Carcinoma of the Large Intestine," Circhows Arch, (2010), 457:433-441.
Levine, Joel S., et al., "Adenomatous Polyps of the Colon," The New England Journal of Medicine, (2006), 355:2551-2557.
Lu, Jun, et al., "MicroRNA Expression Profiles Classify Human Cancers," Nature, vol. 435, Jun. 9, 2005, pp. 834-838.
Mandel, Jack S., et al., "Reducing Mortality from Colorectal Cancer by Screening for Fecal Occult Blood," vol. 328, No. 19, May 13, 1993, pp. 1365-1371.
Meissner, Helen I., et al., "Patterns of Colorectal Cancer Screening Uptake Among Men and Women in the United States," Cancer Epidemiol Biomarkers, (2006), 15:389-394.
Mestdagh, Pieter, et al., "A Novel and Universal Method for MicroRNA RT-qPCR Data Normalization," http:// genomebiology.com/2009/10/6/R64, Genome Biology 2009, vol. 10, Issue 6, Article R64, 10 pages.
Mitchell, Patrick S., et al., "Circulating MicroRNAs as Stable Blood-Based Markers for Cancer Detection," PNAS, vol. 105, No. 30, Jul. 29, 2008, pp. 10513-10518.
Motoyama, Kazuo, et al., "Over-and Under-Expressed MicroRNAs in Human Colorectal Cancer," International Journal of Oncology, (2009), 34:1069-1075.
Nagasaka, Takeshi, et al., "Analysis of Fecal DNA Methylation to Detect Gastrointestinal Neoplasia," J. Natl Cancer Inst., vol. 101, Issue 18, Sep. 16, 2009, pp. 1244-1258.
Ng, Eko, et al., "Differential Expression of MicroRNAs in Plasma of Patients with Colorectal Cancer: A Potential Marker for Colorectal Cancer Screening," Gut, (2009), 58: 1375-1381.
Ogino et al., "A Cohort Study of Tumoral LINE-1 Hypomethylation and Prognosis in Colon Cancer," Brief Communications, JNCI, 2008, vol. 100, issue 23, pp. 1734-1738.
Ouyang, Daniel L., et al., "Noninvasive Testing for Colorectal Cancer: A Review," American Journal of Gastroenterology, (2005), 100(6): 1393-1403.
Pu, X-X, et al. "Circulating miR-221 directly amplified from plasma is a potential diagnostic and prognostic marker of colorectal cancer and is correlated with p53 expression," Journal of Gastroenterology and Hepatology, 2010, vol. 25, pp. 1674-1680.
Rabinowits, Guilherme, et al., "Exosomal MicroRNA: A Diagnostic Marker for Lung Cancer," Clinical Lung Cancer, vol. 10, No. 1, Jan. 2009, pp. 42-46.
Schetter, Aaron J., et al., "MicroRNA Expression Profiles Associated with Prognosis and Therapeutic Outcome in Colon Adenocarcinoma," American Medical Association, vol. 299, No. 4, Jan. 30, 2008, pp. 425-436.
Scott et al., "Molecular Biology of Colorectal Neoplasia," Gut, 1993, vol. 34, pp. 289-292.
Slaby, et al., "Altered expression of miR-21, miR-31, miR-143 and miR-145 is related to clinicopathologic features of colorectal cancer," Oncology. 2007;72(5-6):397-402.
Vandesompele, Jo, et al., "Accurate Normalization of Real-Time Quantitative RT-PCR Data by Geometric Averaging of Multiple Internal Control Genes," Genome Biology, (2002), 12 pages.

(56) References Cited

OTHER PUBLICATIONS

Wang, X. et al. "Spreading of Alu Methylation to the Promoter of the MLH1 Gene in Gastrointestinal Cancer", PLoS One, Oct. 2011, vol. 6, Issue 10, e25913, pp. 1-6.
Youden, "Index for Rating Diagnostic Tests," Cancer, 3: 32-35, 1950.
Zhang, P. et al. "Comprehensive gene and microRNA expression profiling reveals the crucial role of has-let-7i and its target genes in colorectal cancer metastasis", Molecular Biology Reports, 2012, vol. 39, No. 2, pp. 1471-1478, Published online: May 29, 2011.
Zhang, Y. et al. "microRNA-320a inhibits tumor invasion by targeting neuropilin 1 and is associated with liver metastasis in colorectal cancer", Oncology Reports, 2012, vol. 27, pp. 685-694. Published online: Nov. 23, 2011.
Zou, Hongzhi, et al., "High Detection Rates of Colorectal Neoplasia by Stool DNA Testing with a Novel Digital Melt Curve Assay," Gastroenterology, (2009), 136:459-470.
Zweig & Campbell, "Receiver-Operating Characteristic (ROC) Plots: A Fundamental Evaluation Tool in Clinical Medicine," *Clinical Chemistry*, 39: 561-577, 1993.

\* cited by examiner

METHODS FOR DIAGNOSING AND TREATING GASTRIC CANCER USING MIRNA EXPRESSION

This application is a national phase under 35 U.S.C. § 371 of International Application No. PCT/US2018/021713, filed Mar. 9, 2018, which claims the benefit of priority to U.S. Provisional Patent Application Ser. No. 62/469,857, filed Mar. 10, 2017, the entire contents of each of which are hereby incorporated by reference in their entirety.

This invention was made with government support under Grant Nos. R01 CA72851, CA181572, CA184792 and CA202797 awarded by the National Institutes of Health. The government has certain rights in the invention.

BACKGROUND

1. Field of the Invention

The present invention relates generally to the fields of molecular biology and oncology. More particularly, it concerns methods and compositions involving cancer prognosis, diagnosis, and treatment.

2. Description of Related Art

Although endoscopic surveillance accompanied with pathological examination of tissue biopsies remains the gold standard for diagnosing asymptomatic gastric cancer (GC) patients, associated costs and its invasive nature renders it inadequate as a screening approach. Development of less invasive tests are needed for surveillance and detection of early stage GCs—when the disease is still treatable.

SUMMARY OF THE DISCLOSURE

The current disclosure fulfills a need in the art by providing more effective therapeutic treatments and diagnostic methods for gastric cancer based on the expression level of miRNA biomarkers. Accordingly, aspects of the disclosure relates to a method for treating a patient for gastric cancer comprising: administering one or more of surgery, chemotherapy, radiation therapy, chemoradiation, or targeted cancer therapy to the patient, wherein the patient was determined to have differential expression of one or more of miRNAs selected from miR-18a, miR-21, miR-181a, miR-181b, miR-196a, miR-196b, and miR-146b in a biological sample from the patient compared to a control.

Further aspects of the disclosure relate to a method comprising: detecting, from a patient sample, the expression level of one or more miRNAs selected from miR-18a, miR-21, miR-181a, miR-181b, miR-196a, miR-196b, and miR-146b; and comparing the expression level of the detected miRNAs to a control level of expression.

Yet further aspects of the disclosure relate to a method for determining whether a patient has gastric cancer, the method comprising: determining that the patient has or is at high risk of having gastric cancer when one or more miRNAs selected from miR-18a, miR-21, miR-181a, miR-181b, miR-196a, miR-196b, and miR-146b are determined to be differentially expressed in a biological sample from the patient compared to a control; or determining that the patient does not have or is low risk of having gastric cancer when one or more miRNAs selected from miR-18a, miR-21, miR-181a, miR-181b, miR-196a, miR-196b, and miR-146b are determined to be not significantly different in expression in a biological sample from the patient compared to a control.

In some embodiments, the patient was determined to have increased expression of the one or more miRNAs in the biological sample from the patient compared to a control. In some embodiments, the patient was determined to have decreased expression of the one or more miRNAs in the biological sample from the patient compared to a control.

In some embodiments, the method further comprises comparing the expression level of the miRNA in the biological sample from the patient to the expression level of the same miRNA in a control biological sample. In some embodiments, the expression level is normalized.

In some embodiments, the biological sample from the patient comprises a blood sample. In some embodiments, the biological sample from the patient comprises a serum or plasma fraction of a blood sample. In some embodiments, the biological sample from the patient comprises a biological material described herein. In some embodiments, the control comprises normal mucosa tissues. In some embodiments, the control comprises the level of expression of the miRNAs in a serum sample from a patient determined to not have cancer. In some embodiments, the control comprises the level of expression of the miRNAs in a serum sample from a patient determined to not have gastric cancer.

In some embodiments, the chemotherapy comprises one or more of 5-fluorouracil, capecitabine, carboplatin, cisplatin, docetaxel, epirubicin, irinotecan, oxaliplatin, or paclitaxel. In some embodiments, the chemotherapy comprises one or more chemotherapeutic agents described herein. In some embodiments, the chemotherapy excludes one or more chemotherapeutic agents described herein.

In some embodiments, the method further comprises surgical resection of the primary tumor or metastatic tumor. In some embodiments, the method comprises neo-adjuvant or adjuvant therapy. In some embodiments, the method excludes neo-adjuvant or adjuvant therapy.

In some embodiments, the patient does not have and/or has not been diagnosed with gastric cancer. In some embodiments, the patient has not undergone any other diagnostic procedure for gastric cancer. In some embodiments, the patient does not have a genetic history of gastric cancer. The term "a genetic history" may refer to a familial history of gastric cancer or a determination of a genetic mutation or gene that increases the patient's likelihood of having or acquiring gastric cancer. In some embodiments, the patient has or has been determined to have a genetic predisposition to gastric cancer. In some embodiments, the patient has or has been determined to have a familial history of gastric cancer. In some embodiments, the patient has not reported any symptoms of gastric cancer. In some embodiments, the patient has reported gastric disruptions such as heartburn and/or indigestion.

In some embodiments, the method further comprises calculating a risk score based on the expression levels of the miRNAs in the biological sample from the patient. In some embodiments, the risk score is compared to a cut-off value.

In some embodiments, the patient was determined to have differential expression of miR-18a, miR-21, miR-181a, miR-181b, miR-196a, miR-196b, and miR-146b. In some embodiments, the patient was determined to have differential expression of miR-18a, miR-181b, and miR-196b.

In some embodiments, the method further comprises comparing the expression level of the miRNA in a biological sample from the patient to the expression level of the miRNAs to a control. In some embodiments, the method further comprises measuring the expression level of the miRNAs in a biological sample from the patient.

In some embodiments of the methods of the disclosure, the method further comprises administering a gastric cancer treatment to the patient determined to have or to be at high risk for gastric cancer. In some embodiments, the method further comprises performing an additional diagnostic method to the patient determined to have or to be at high risk for gastric cancer.

In some embodiments, the method further comprises predicting that the patient is likely to survive, likely to have disease free survival, and/or likely to have recurrence free survival when the expression level of the miRNA in the biological sample from the patient is not significantly different than the expression level of the miRNA in a control.

In some embodiments, the method comprises determining that the patient has or is at high risk of having gastric cancer when miR-18a, miR-21, miR-181a, miR-181b, miR-196a, miR-196b, and miR-146b are determined to be differentially expressed in a biological sample from the patient compared to a control; or determining that the patient does not have or is low risk of having gastric cancer when miR-18a, miR-21, miR-181a, miR-181b, miR-196a, miR-196b, and miR-146b are determined to be not significantly different in expression in a biological sample from the patient compared to a control.

In some embodiments, the method comprises determining that the patient has or is at high risk of having gastric cancer when miR-18a, miR-181b, and miR-196b are determined to be differentially expressed in a biological sample from the patient compared to a control; or determining that the patient does not have or is low risk of having gastric cancer when miR-18a, miR-181b, and miR-196b are determined to be not significantly different in expression in a biological sample from the patient compared to a control. In some embodiments, the patient diagnosed with high risk is identified as one likely to have or develop distant metastasis, liver metastasis, and/or lymph node metastasis.

In some embodiments, the patient has, is determined to have, or is diagnosed with stage I, II, III, or IV gastric cancer. In some embodiments, the patient was determined to have stage I, II, III, or IV gastric cancer on the basis of a clinical measurement or biomarker measurement described herein. In some embodiments, the patient is diagnosed with Stage I or II gastric cancer and does not have lymph node metastasis. In some embodiments, the patient diagnosed with high risk is identified as one likely to have or develop distant metastasis, liver metastasis, and/or lymph node metastasis. In some embodiments, the patient diagnosed with high risk is identified as one likely to develop chemoresistance.

The expression level or activity level from a control sample may be an average value, a normalized value, a cut-off value, or an average normalized value. The expression level or activity level may be an average or mean obtained from a significant proportion of patient samples. The expression or activity level may also be an average or mean from one or more samples from the patient.

In some embodiments, the method further comprises surgical incision of the primary tumor. In some embodiments, the elevated level/increased expression or reduced level/decreased expression is at least 1, 1.5, 2, 2.5, 3, 3.5, 4, 4.5, 5, 5.5, 6, 7, 8, 9, 10, 12, 14, 16, 18, 20, 50, 100, 150, 200, 250, 500, or 1000 fold (or any derivable range therein) or at least 10, 20, 30, 40, 50, 60, 70, 80, 90, 100, 200, 300, 400, 500, 600, 700, 800, or 900% different than the control, or any derivable range therein. In some embodiments, a level of expression may be qualified as "low" or "high," which indicates the patient expresses a certain gene at a level relative to a reference level or a level with a range of reference levels that are determined from multiple samples meeting particular criteria. The level or range of levels in multiple control samples is an example of this. In some embodiments, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. Moreover, the threshold level may be derived from a cohort of individuals meeting a particular criteria. The number in the cohort may be, be at least, or be at most 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 700, 800, 900, 1000, 1100, 1200, 1300, 1400, 1500, 1600, 1700, 1800, 1900, 2000 or more (or any range derivable therein).

In some embodiments, the control may be the average level of expression of the miRNA in a biological sample from a subject having gastric cancer or determined to be at risk for gastric cancer. The control may be the level of expression of the miRNA in a biological sample from a subject with stage I, II, III, or IV gastric cancer (or any TMN stage defined herein). One skilled in the art would understand that, when comparing the expression level of the miRNA in a biological sample from a test subject to the expression level from a subject with gastric cancer, the decision to treat the subject for gastric cancer or diagnose or provide a prognosis that the subject has or is likely to get gastric cancer is based on the a level of expression that is similar to the control or within 1, 2, 3, 4, or 5 deviations or differs by less than 1, 3, 5, 10, 15, 20, 30, or 40% (or any derivable range therein).

In some embodiments, the biological sample from the patient is a sample from a primary gastric cancer tumor. In some embodiments, the biological sample is from a tissue or organ as described herein. In still further embodiments, the method may comprise obtaining a sample of the subject or patient. Non-limiting examples of the sample include a tissue sample, a whole blood sample, a urine sample, a saliva sample, a serum sample, a plasma sample, or a fecal sample. In particular embodiments, the sample is a serum sample, a plasma sample or a whole blood sample.

In some embodiments the subject or patient is one that has previously been treated for gastric cancer. In some embodiments, the gastric cancer is recurrent.

The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy.

In certain embodiments the sample is obtained from a biopsy from intestinal, stomach, or other associated gastric tissues. In other embodiments the sample may be obtained from any of the tissues provided herein that include but are not limited to gall bladder, skin, heart, lung, breast, pancreas, liver, muscle, kidney, smooth muscle, bladder, intestine, brain, prostate, esophagus, or thyroid tissue.

In certain aspects the sample is obtained from cystic fluid or fluid derived from a tumor or neoplasm. In yet other embodiments the cyst, tumor or neoplasm is in the digestive system. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. Further embodiments include isolating or analyzing protein expression in a biological sample for the expression of the biomarker.

In certain embodiments, a microarray may be used to measure or assay the level of the biomarkers in a sample. The methods may further comprise recording the biomarker expression or activity level in a tangible medium or reporting the expression or activity level to the patient, a health care payer, a physician, an insurance agent, or an electronic system.

In some embodiments, methods will involve determining or calculating a prognosis score based on data concerning the expression or activity level of one or more of the biomarkers, meaning that the expression or activity level of one or more of the biomarkers is at least one of the factors on which the score is based. A prognosis score will provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor response to a particular treatment. Alternatively, the probability may be expressed generally in percentiles, quartiles, or deciles.

A difference between or among weighted coefficients or expression or activity levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression or activity levels in a biomarker, gene, or protein.

Further aspects relate to a kit comprising nucleic acid probes for detecting the expression level of differentially expressed miRNAs in a biological sample; wherein the differentially expressed miRNAs comprise one or more of: miR-18a, miR-21, miR-181a, miR-181b, miR-196a, miR-196b, and miR-146b. In some embodiments, the differentially expressed miRNAs consist of miR-18a, miR-21, miR-181a, miR-181b, miR-196a, miR-196b, and miR-146b. In some embodiments, the differentially expressed miRNAs consist of miR-18a, miR-181b, and miR-196b. In some embodiments, the probes are labeled. In some embodiments, the kit further comprises nucleic acid probes for detecting a control. In some embodiments, the control comprises a RNA, miRNA, or protein not differentially expressed in gastric cancer. In some embodiments, the probe comprises nucleic acid primers that are capable of amplifying the RNA or a cDNA made from the RNA by PCR. In some embodiments, the kit further comprises reagents for performing one or more of reverse transcriptase PCR, DNA amplification by PCR, and real-time PCR. In some embodiments, the kit further comprises instructions for use.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression or activity level of a gene, biomarker or protein in a sample from a patient; and b) determining a difference value in the expression or activity levels using the information corresponding to the expression or activity levels in the sample compared to a control or reference expression or activity level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for gastric cancer, administering the same treatment as the first treatment to the patient if the patient does not have increased expression or activity level; administering a different treatment from the first treatment to the patient if the patient has increased expression or activity level.

In some embodiments, receiving information comprises receiving from a tangible data storage device information corresponding to the expression or activity levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional gastric cancer therapy if the patient does not have expression or activity levels, and/or or treating the patient with an alternative gastric cancer therapy if the patient has increased expression or activity levels.

The tangible, computer-readable medium further comprise computer-readable code that, when executed by a computer, causes the computer to perform one or more additional operations comprising calculating a prognosis score for the patient. The operations may further comprise making recommendations comprising: administering a treatment comprising a thymidylate synthase inhibitor to a patient that is determined to have a decreased expression or activity level.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Early-stage stomach cancer is difficult to detect, since it rarely causes any symptoms. Unfortunately, the cost an invasiveness of available detection techniques for gastric cancer make them ineffective as a routine screening procedure. The current disclosure provides techniques that can be used in a routine screen to detect gastric cancer in its earliest stages, when treatment options are optimal. The methods of the current disclosure are minimally invasive and less expensive. Thus, the current disclosure provides novel screening and therapeutic regimens that improve the detection and treatment of gastric cancer.

I. DEFINITIONS

As used herein, the term "antibody" encompasses antibodies and antibody fragments thereof, derived from any antibody-producing mammal (e.g., mouse, rat, rabbit, and primate including human), that specifically bind to an antigenic polypeptide. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

"Prognosis" refers to as a prediction of how a patient will progress, and whether there is a chance of recovery. "Cancer prognosis" generally refers to a forecast or prediction of the probable course or outcome of the cancer, with or without a treatment. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis also includes prediction of favorable responses to cancer treatments, such as a conventional cancer therapy. A response may be either a therapeutic response (sensitivity or recurrence-free survival) or a lack of therapeutic response (residual disease, which may indicate resistance or recurrence).

The term substantially the same or not significantly different refers to a level of expression that is not significantly different than what it is compared to. Alternatively, or in conjunction, the term substantially the same refers to a level of expression that is less than 2, 1.5, or 1.25 fold different than the expression or activity level it is compared to.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

The term "disease free survival" is a clinical endpoint and is usually used to analyze the results of the treatment for the localized disease which renders the patient apparently disease free, such as surgery or surgery plus adjuvant therapy. In the disease-free survival, the event is relapse rather than death. The people who relapse are still surviving but they are no longer disease-free. Just as in the survival curves not all patients die, in "disease-free survival curves" not all patients relapse and the curve may have a final plateau representing the patients who didn't relapse after the study's maximum follow-up. Because the patients survive for at least some time after the relapse, the curve for the actual survival would look better than disease free survival curve.

The term "primer" or "probe" as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased expression" or "elevated expression" or "decreased expression" refers to an expression level of a biomarker (i.e. the miRNAs described herein) in the subject's sample as compared to a reference level representing the same biomarker or a different biomarker. In certain aspects, the reference level may be a reference level of expression from a non-cancerous tissue from the same subject. Alternatively, the reference level may be a reference level of expression from a different subject or group of subjects. For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer. The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that an numerical value discussed herein may be used with the term "about" or "approximately."

II. GASTRIC CANCER STAGING AND TREATMENTS

Methods and compositions may be provided for treating gastric cancer with particular applications of miRNA expression or activity levels. Based on a profile of miRNA expression or activity levels, different treatments may be prescribed or recommended for different cancer patients.

A. Cancer Staging

Gastric cancer, also known as stomach cancer tends to develop slowly over many years. Before a true cancer develops, pre-cancerous changes often occur in the inner lining (mucosa) of the stomach. These early changes rarely cause symptoms and therefore often go undetected.

Cancers starting in different sections of the stomach may cause different symptoms and tend to have different outcomes. The cancer's location can also affect the treatment options. For example, cancers that start at the gastroesophageal (GE) junction are staged and treated the same as cancers of the esophagus. A cancer that starts in the cardia of the stomach but then grows into the GE junction is also staged and treated like a cancer of the esophagus.

Stomach cancers can spread (metastasize) in different ways. They can grow through the wall of the stomach and invade nearby organs. They can also spread to the lymph vessels and nearby lymph nodes. Lymph nodes are bean-sized structures that help fight infections. The stomach has a very rich network of lymph vessels and nodes. As the stomach cancer becomes more advanced, it can travel through the bloodstream and spread to organs such as the liver, lungs, and bones. If cancer has spread to the lymph nodes or to other organs, the patient's outlook is not as good.

Different types of stomach cancer include: adenocarcinomas, lymphomas, gastrointestinal stromal tumor (GIST), and carcinoid tumor. Squamous cell carcinoma, small cell carcinoma, and leiomyosarcoma, can also start in the stomach, but these cancers are very rare.

The most common staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome. Details of this system are in the tables below:

| T categories of stomach cancer | T0: No signs of a main tumor can be found.<br>Tis: Cancer cells are only in the top layer of cells of the mucosa (innermost layer of the stomach) and have not grown into deeper layers of tissue such as the lamina propria or muscularis mucosa. This stage is also known as carcinoma in situ.<br>T1: The tumor has grown from the top layer of cells of the mucosa into the next layers below such as the lamina propria, the muscularis mucosa, or submucosa.<br>T1a: The tumor is growing into the lamina propria or muscularis mucosa.<br>T1b: The tumor has grown through the lamina propria and muscularis mucosa and into the submucosa.<br>T2: The tumor is growing into the muscularis propria layer.<br>T3: The tumor is growing into the subserosa layer.<br>T4: The tumor has grown into the serosa and may be growing into a nearby organ (spleen, intestines, pancreas, kidney, etc.) or other structures such as major blood vessels.<br>T4a: The tumor has grown through the stomach wall into the serosa, but the cancer hasn't grown into any of the nearby organs or structures. |
|---|---|

| | |
|---|---|
| N categories of stomach cancer | T4b: The tumor has grown through the stomach wall and into nearby organs or structures.<br>N0: No spread to nearby lymph nodes.<br>N1: The cancer has spread to 1 to 2 nearby lymph nodes.<br>N2: The cancer has spread to 3 to 6 nearby lymph nodes.<br>N3: The cancer has spread 7 or more nearby lymph nodes.<br>N3a: The cancer has spread to 7 to 15 nearby lymph nodes.<br>N3b: The cancer has spread to 16 or more nearby lymph nodes. |
| M categories of stomach cancer | M0: No distant metastasis (the cancer has not spread to distant organs or sites, such as the liver, lungs, or brain).<br>M1: Distant metastasis (the cancer has spread to organs or lymph nodes far away from the stomach). |

| AJCC stage | TNM stage |
|---|---|
| Stage 0 | Tis N0 M0 |
| Stage I-A | T1 N0 M0 |
| Stage I-B | T1, N1, M0; or T2, N0, M0 |
| Stage II-A | T1, N2, M0; or T2, N1, M0; or T3, N0, M0 |
| Stage II-B | T1, N3, M0; or T2, N2, M0; or T3, N1, M0; or T4a, N0, M0 |
| Stage III-A | T2, N3, M0; or T3, N2, M0; or T4a, N1, M0 |
| Stage III-B | T3, N3, M0; or T4a, N2, M0; or T4b, N0 or N1, M0 |
| Stage III-C | T4a, N3, M0; or T4b, N2 or N3, M0 |
| Stage IV | Any T, any N, M1 |

The "cancer" referred to in the methods described herein may include or exclude any of the above stages or TNM categories.

B. Therapy

For a very early stage (T1a) cancer, some doctors may recommend a non-surgical treatment called endoscopic mucosal resection. This is the removal of the tumor with an endoscope. In early stages (stages 0 or I), when the cancer is still only in the stomach, surgery is used to remove the part of the stomach with cancer and nearby lymph nodes. This is called a subtotal or partial gastrectomy. In a partial gastrectomy, the surgeon connects the remaining part of the stomach to the esophagus or small intestine.

If the cancer has spread to the outer stomach wall with or without having spread to the lymph nodes, surgery plus chemotherapy or chemotherapy and radiation therapy may be used. The surgeon can perform a subtotal gastrectomy or a total gastrectomy, which is the removal of all of the stomach. During a total gastrectomy, the surgeon attaches the esophagus directly to the small intestine. Regional lymph nodes are often removed during surgery because the cancer may have spread to those lymph nodes. This is called a lymphadenectomy.

Radiation therapy is the use of high-energy x-rays or other particles to destroy cancer cells. A radiation therapy regimen may comprise a specific number of treatments given over a set period of time. Patients with stomach cancer usually receive external-beam radiation therapy, which is radiation given from a machine outside the body. Radiation therapy may be used before surgery to shrink the size of the tumor or after surgery to destroy any remaining cancer cells.

Chemotherapy is the use of drugs to destroy cancer cells, usually by stopping the cancer cells' ability to grow and divide. Chemotherapy is given by a medical oncologist. Systemic chemotherapy gets into the bloodstream to reach cancer cells throughout the body. Common ways to give chemotherapy include an intravenous (IV) tube placed into a vein using a needle or in a pill or capsule that is swallowed (orally). A chemotherapy regimen usually comprises a specific number of cycles given over a set period of time. A patient may receive 1 drug at a time or combinations of different drugs at the same time.

The goal of chemotherapy can be to destroy cancer remaining after surgery, slow the tumor's growth, or reduce cancer-related symptoms. It also may be combined with radiation therapy. Exemplary chemotherapeutic regimens include, for example, the combination of fluorouracil (5-FU, Adrucil) and cisplatin (Platinol). Newer drugs similar to 5-FU, such as capecitabine (Xeloda), and similar to cisplatin, such as oxaliplatin (Eloxatin), appear to work equally well. Other drugs commonly used include docetaxel (Docefrez, Taxotere), epirubicin (Ellence), irinotecan (Camptosar), and paclitaxel (Taxol).

Antimetabolites can be used in cancer treatment, as they interfere with DNA production and therefore cell division and the growth of tumors. Because cancer cells spend more time dividing than other cells, inhibiting cell division harms tumor cells more than other cells. Anti-metabolites masquerade as a purine (azathioprine, mercaptopurine) or a pyrimidine, chemicals that become the building-blocks of DNA. They prevent these substances becoming incorporated in to DNA during the S phase (of the cell cycle), stopping normal development and division. They also affect RNA synthesis. However, because thymidine is used in DNA but not in RNA (where uracil is used instead), inhibition of thymidine synthesis via thymidylate synthase selectively inhibits DNA synthesis over RNA synthesis. Due to their efficiency, these drugs are the most widely used cytostatics. In the ATC system, they are classified under L01B.

Thymidylate synthase inhibitors are chemical agents which inhibit the enzyme thymidylate synthase and have potential as an anticancer chemotherapy. As an anti-cancer chemotherapy target, thymidylate synthetase can be inhibited by the thymidylate synthase inhibitors such as fluorinated pyrimidine fluorouracil, or certain folate analogues, the most notable one being raltitrexed (trade name Tomudex). Additional agents include pemetrexed, nolatrexed, ZD9331, and GS7904L.

In further embodiments, there may be involved prodrugs that can be converted to thymidylate synthase inhibitors in the body, such as Capecitabine (INN), an orally-administered chemotherapeutic agent used in the treatment of numerous cancers. Capecitabine is a prodrug, that is enzymatically converted to 5-fluorouracil in the body.

If cancer has entered the lymph nodes, adding the chemotherapy agents fluorouracil or capecitabine increases life expectancy. Chemotherapy agents for this condition may include capecitabine, fluorouracil, irinotecan, leucovorin, oxaliplatin and UFT. Another type of agent that is sometimes used are the epidermal growth factor receptor inhibitors.

In certain embodiments, alternative treatments may be prescribed or recommended based on the biomarker profile. In addition to traditional chemotherapy for gastric cancer patients, cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Just as for chemotherapy, radiotherapy can be used in the neoadjuvant and adjuvant setting for some stages of gastric cancer.

Targeted therapy may also be used in the methods described herein. Targeted therapy is a treatment that targets the cancer's specific genes, proteins, or the tissue environment that contributes to cancer growth and survival. This type of treatment blocks the growth and spread of cancer cells while limiting damage to healthy cells. In some embodiments, the doctor may run tests to identify the genes, proteins, and other factors in your tumor. This helps doctors better match each patient with the most effective treatment whenever possible.

In some embodiments, the methods further comprise testing a biological sample from the patient for HER2 expression. In some embodiments, the patients with HER2-positive stomach cancer are treated with trastuzumab (Herceptin) In some embodiments, this is in combination with chemotherapy. Herceptin is one type of HER2-targeted therapy. For patients with metastatic or recurrent gastroesophageal cancer that is HER2 positive, ASCO, ASCP, and CAP recommend a combination of chemotherapy and HER2-targeted therapy. If the cancer is HER2 negative, HER2-targeted therapy is not a treatment option for you, and your doctor will give you other options for treating the cancer.

For patients whose tumor has grown while receiving initial chemotherapy, the drug called ramucirumab (Cyramza) may be used as an additional treatment. Ramucirumab is a type of targeted therapy called an anti-angiogenic. It is focused on stopping angiogenesis, which is the process of making new blood vessels. Because a tumor needs the nutrients delivered by blood vessels to grow and spread, the goal of anti-angiogenesis therapies is to "starve" the tumor.

Immunotherapies that are designed to boost the body's natural defenses to fight the cancer may also be used. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting.

In yet another embodiment, the treatment is a gene therapy. In certain embodiments, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell. Examples of tumor suppressor nucleic acids within this definition include, but are not limited to APC, CYLD, HIN-I, KRAS2b, pl6, pl9, p21, p27, p27mt, p53, p57, p73, PTEN, Rb, Uteroglobin, Skp2, BRCA-I, BRCA-2, CHK2, CDKN2A, DCC, DPC4, MADR2/JV18, MEN1, MEN2, MTS1, NF1, NF2, VHL, WRN, WT1, CFTR, C-CAM, CTS-I, zacl, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at www.cise.ufl.edu/~yy1/HTML-TSGDB/Homepage.litml. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied.

The methods described herein may include or exclude any of the cancer therapies described in the disclosure.

C. Monitoring

In certain aspects, the miRNA-based method may be combined with one or more other gastric cancer diagnosis or screening tests at increased frequency if the patient is determined to be at high risk for recurrence or have a poor prognosis based on the miRNA described above.

The monitoring protocol may include any methods known in the art. In particular, the monitoring include obtaining a sample and testing the sample for diagnosis. For example, the monitoring may include endoscopy, biopsy, endoscopic ultrasound, X-ray, barium swallow, a Ct scan, a MRI, a PET scan, laparoscopy, or HER2 testing.

D. ROC Analysis

In statistics, a receiver operating characteristic (ROC), or ROC curve, is a graphical plot that illustrates the performance of a binary classifier system as its discrimination threshold is varied. The curve is created by plotting the true positive rate against the false positive rate at various threshold settings. (The true-positive rate is also known as sensitivity in biomedical informatics, or recall in machine learning. The false-positive rate is also known as the fall-out and can be calculated as 1−specificity). The ROC curve is thus the sensitivity as a function of fall-out. In general, if the probability distributions for both detection and false alarm are known, the ROC curve can be generated by plotting the cumulative distribution function (area under the probability distribution from −infinity to +infinity) of the detection probability in the y-axis versus the cumulative distribution function of the false-alarm probability in x-axis.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

The ROC curve was first developed by electrical engineers and radar engineers during World War II for detecting enemy objects in battlefields and was soon introduced to psychology to account for perceptual detection of stimuli. ROC analysis since then has been used in medicine, radiology, biometrics, and other areas for many decades and is increasingly used in machine learning and data mining research.

The ROC is also known as a relative operating characteristic curve, because it is a comparison of two operating characteristics (TPR and FPR) as the criterion changes. ROC analysis curves are known in the art and described in Metz C E (1978) Basic principles of ROC analysis. Seminars in Nuclear Medicine 8:283-298; Youden W J (1950) An index for rating diagnostic tests. Cancer 3:32-35; Zweig M H, Campbell G (1993) Receiver-operating characteristic (ROC) plots: a fundamental evaluation tool in clinical medicine. Clinical Chemistry 39:561-577; and Greiner M, Pfeiffer D, Smith R D (2000) Principles and practical application of the receiver-operating characteristic analysis for diagnostic tests. Preventive Veterinary Medicine 45:23-41, which are herein incorporated by reference in their entirety.

III. SAMPLE PREPARATION

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from intestinal or mucosal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is gastric. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple samples may be obtained for diagnosis by the methods described herein. In other cases, multiple samples, such as one or more samples from one tissue type (for example serum) and one or more samples from another tissue (for example gastric) may be obtained for diagnosis by the methods. In some cases, multiple samples such as one or more samples from one tissue type (e.g. gastric) and one or more samples from another tissue (e.g. serum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a gastric or a suspected gastric tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

IV. NUCLEIC ACID ASSAYS

Aspects of the methods include assaying nucleic acids to determine expression or activity levels. Arrays can be used to detect differences between two samples. Specifically contemplated applications include identifying and/or quantifying differences between RNA from a sample that is normal and from a sample that is not normal, between a cancerous condition and a non-cancerous condition, or between two differently treated samples. Also, RNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may be or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes.

In addition to the use of arrays and microarrays, it is contemplated that a number of difference assays could be employed to analyze nucleic acids, their activities, and their effects. Such assays include, but are not limited to, nucleic amplification, polymerase chain reaction, quantitative PCR, RT-PCR, in situ hybridization, Northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

A further assay useful for quantifying and/or identifying nucleic acids is RNAseq. RNA-seq (RNA sequencing), also called whole transcriptome shotgun sequencing, uses next-generation sequencing (NGS) to reveal the presence and quantity of RNA in a biological sample at a given moment in time. RNA-Seq is used to analyze the continually changing cellular transcriptome. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

V. PROTEIN ASSAYS

A variety of techniques can be employed to measure expression levels of polypeptides and proteins in a biological sample. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining protein expression levels of biomarkers.

In one embodiment, antibodies, or antibody fragments or derivatives, can be used in methods such as Western blots or immunofluorescence techniques to detect biomarker expression. In some embodiments, either the antibodies or proteins are immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present disclosure. The support can then be washed with suitable buffers followed by treatment with the detectably labeled antibody. The solid phase support can then be washed with the buffer a second time to remove unbound antibody. The amount of bound label on the solid support can then be detected by conventional means.

Immunohistochemistry methods are also suitable for detecting the expression levels of biomarkers. In some embodiments, antibodies or antisera, including polyclonal antisera, and monoclonal antibodies specific for each marker may be used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art. A two-site, monoclonal-based immunoassay utilizing antibodies reactive to two non-interfering epitopes or a competitive binding assay may be employed.

Numerous labels are available and commonly known in the art. Radioisotope labels include, for example, $^{36}S$, $^{14}C$, $^{125}I$, $^{3}H$, and $^{131}I$. The antibody can be labeled with the radioisotope using the techniques known in the art. Fluorescent labels include, for example, labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques known in the art. Fluorescence can be quantified using a fluorimeter. Various enzyme-substrate labels are available and U.S. Pat. Nos. 4,275,149, 4,318,980 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzymology (Ed. J. Langone & H. Van Vunakis), Academic press, New York, 73:147-166(1981).

In some embodiments, a detection label is indirectly conjugated with an antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). In some embodiments, the antibody need not be labeled, and the presence thereof can be detected using a labeled antibody, which binds to the antibody.

VI. PHARMACEUTICAL COMPOSITIONS

In certain aspects, the compositions or agents for use in the methods, such as chemotherapeutic agents or biomarker modulators, are suitably contained in a pharmaceutically acceptable carrier. The carrier is non-toxic, biocompatible and is selected so as not to detrimentally affect the biological activity of the agent. The agents in some aspects of the disclosure may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antgifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VII. KITS

Certain aspects of the present disclosure also concern kits containing compositions of the disclosure or compositions to implement methods of the disclosure. In some embodiments, kits can be used to evaluate one or more nucleic acid and/or polypeptide molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more nucleic acid probes, synthetic RNA molecules or inhibitors, or any value or range and combination derivable therein. In some embodiments, there are kits for evaluating biomarker levels or activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, polypeptide detecting agents, and/or inhibitors or antagonists of the disclosure for prognostic or diagnostic applications are included. Specifically contemplated are any such molecules corresponding to any biomarker nucleic acid or polypeptide.

In certain aspects, negative and/or positive control agents are included in some kit embodiments. The control molecules can be used to verify efficiency and/or control for sample quality or to normalize expression.

It is contemplated that any method or composition described herein can be implemented with respect to any other method or composition described herein and that different embodiments may be combined.

Any embodiment of the disclosure relating to a polypeptide or nucleic acid is contemplated also to cover embodiments whose sequences are at least 80, 81, 82, 83, 84, 85, 86, 87, 88, 89, 90, 91, 92, 93, 94, 95, 96, 97, 98, 99% identical to the polypeptide or nucleic acid.

Embodiments of the disclosure include kits for analysis of a pathological sample by assessing a nucleic acid or polypeptide profile for a sample comprising, in suitable container means, two or more RNA probes, or a biomarker polypeptide detecting agent, wherein the RNA probes or polypeptide detecting agent detects biomarker nucleic acids or polypeptides. In some embodiments, the reagents (i.e. RNA probe and/or polypeptide detecting agent) are labeled with a detectable label. Labels are known in the art and also described herein. The kit can further comprise reagents for labeling probes, nucleic acids, and/or detecting agents. The kit may also include labeling reagents, including at least one of amine-modified nucleotide, poly(A) polymerase, and poly(A) polymerase buffer. Labeling reagents can include an amine-reactive dye.

VIII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Identification, Development and Validation of a Circulating miRNA-Based Diagnostic Signature for Early Detection of Gastric Cancer Herein, for the first time, the inventors have conducted a comprehensive miRNA expression profiling, followed by bioinformatic and statistical analysis to establish a novel serum-based miRNA signature for the diagnosis of patients with gastric cancer.

Tissue miRNA expression profiles were analyzed in three patient cohorts (TCGA: n=477; GSE23739: n=82 and GSE33743: n=43) in an in-silico discovery step, during which the robustness of candidate biomarkers was tested and validated. The expression of this miRNA panel was subsequently examined in 50 matched pairs of gastric cancer and normal mucosa tissues. The performance of this miRNA signature was evaluated in a serum training cohort of 268 patients (GC=218; endoscopically negative patients (ENP)=50). Using a stepwise logistic regression model, the panel was further refined to accommodate for differences between tissue and serum miRNA expression levels, and this circulating miRNA signature was validated in another independent 359 patient cohort (GC=292; ENP=67).

Initial in silico candidate selection resulted in the identification of 7 differentially expressed miRNAs in GC patients (miR-18a, 21, 181a, 181b, 196a, 196b, 146b), and a combined expression panel yielded remarkable robustness for distinguishing GC vs. normal mucosa tissues (AUC=1). These results were validated in two independent publicly available datasets (TCGA: AUC=0.94, GSE33743: AUC=0.97), as well as GC tissues (AUC=0.98). The performance of this 7-miRNA panel was next examined in a serum training cohort, and this panel was refined to include three miRNAs (miR-18a, 181b, 196b: AUC=0.87, sensitivity=87.6%, specificity=70.0%). The inventors thereafter successfully evaluated and validated the performance of this panel in an independent patient cohort (AUC=0.82). Intriguingly, this panel distinguished Stage-I GC patients from ENP (AUC=0.80) indicating its effectiveness and clinical usefulness for noninvasive detection of GC. Furthermore, it was discovered that this signature was significantly superior in distinguishing GC from ENP, compared to conventional clinical tumor markers, CEA and CA19-9.

Using a systematic and comprehensive biomarker discovery, prioritization and validation approach, the inventors for the first time, have identified and developed a novel serum-based miRNA signature that offers a promise for noninvasive, early detection of gastric cancer.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and the publications referred to throughout the specification, to the extent that they provide exemplary procedural or other details supplementary to those set forth herein, are specifically incorporated herein by reference.

What is claimed is:

1. A method for treating a patient for gastric cancer comprising: administering a gastric cancer treatment to the patient, wherein a biological sample from the patient has been assayed for the expression level of micro RNA molecules and an elevated level of expression has been detected for a group of micro RNA molecules consisting of: miR-18a, miR-21, miR-181a, miR-181b, miR-196a, miR-196b, and miR-146b, relative to the expression level of a same group of micro RNA molecules in a control biological sample, and wherein the gastric cancer treatment includes one or more of surgery, chemotherapy, or radiation therapy.

2. The method of claim 1, wherein the elevated level of expression is normalized.

3. The method of claim 1, wherein the biological sample from the patient comprises a blood sample.

4. The method of claim 3, wherein the biological sample from the patient comprises a serum or plasma fraction of a blood sample.

5. The method of claim 1, wherein the control biological sample comprises normal mucosa tissues.

6. The method of claim 1, wherein the control biological sample comprises the level of expression of the same group of micro RNA molecules in a serum sample from a patient determined to not have cancer.

7. The method of claim 6, wherein the control biological sample comprises the level of expression of the same group of micro RNA molecules in a serum sample from a patient determined to not have gastric cancer.

8. The method of claim 1, wherein the chemotherapy comprises one or more of 5-fluorouracil, capecitabine, carboplatin, cisplatin, docetaxel, epirubicin, irinotecan, oxaliplatin, or paclitaxel.

9. The method of claim 1, wherein the surgery comprises surgical resection of the primary tumor or metastatic tumor.

* * * * *